US012788709B2

(12) United States Patent
Oger et al.

(10) Patent No.: US 12,788,709 B2
(45) **Date of Patent: *Nov. 10, 2026**

(54) BLACK TEA LEAF EXTRACT, COMPOSITIONS CONTAINING SAME, AND COSMETIC USES THEREOF

(71) Applicant: ISP INVESTMENTS LLC, Wilmington, DE (US)

(72) Inventors: Elodie Oger, Antibes (FR); Laura Mouret, Biot (FR)

(73) Assignee: ISP INVESTMENTS LLC, Wilmington, DE (US)

( * ) Notice: Subject to any disclaimer, the term of this patent is extended or adjusted under 35 U.S.C. 154(b) by 282 days.

This patent is subject to a terminal disclaimer.

(21) Appl. No.: 18/291,098

(22) PCT Filed: Jul. 19, 2022

(86) PCT No.: PCT/EP2022/070181

§ 371 (c)(1),
(2) Date: Jan. 22, 2024

(87) PCT Pub. No.: WO2023/001812

PCT Pub. Date: Jan. 26, 2023

(65) Prior Publication Data

US 2024/0374503 A1 Nov. 14, 2024

(30) Foreign Application Priority Data

Jul. 22, 2021 (FR) ....................................... 2107927

(51) Int. Cl.
*A61K 8/9789* (2017.01)
*A61Q 17/04* (2006.01)
(Continued)

(52) U.S. Cl.
CPC ............ *A61K 8/9789* (2017.08); *A61Q 17/04* (2013.01); *A61Q 19/007* (2013.01); *A61Q 19/02* (2013.01); *A61Q 19/08* (2013.01)

(58) Field of Classification Search
CPC .... A61K 8/9789; A61Q 17/04; A61Q 19/007; A61Q 19/02; A61Q 19/08
See application file for complete search history.

(56) References Cited

U.S. PATENT DOCUMENTS

2017/0312216 A1 11/2017 Kim et al.
2020/0129579 A1 4/2020 Liao et al.

FOREIGN PATENT DOCUMENTS

EP 0267630 3/1992
JP 2006-191924 A 7/2006
(Continued)

OTHER PUBLICATIONS

References cited on PCT application No. PCT/EP2022/070181 filed on Jul. 19, 2022.

(Continued)

*Primary Examiner* — Blessing M Fubara
(74) *Attorney, Agent, or Firm* — Aseem Mehta; Nathalie Tietcheu

(57) ABSTRACT

The invention relates to an extract of black tea (*Camellia sinensis*) enriched in particular in small RNAs, sugars, phenolic compounds, amino acids and theanine, and to a process for preparing such an extract. The invention also relates to cosmetic compositions comprising such an extract, and to the uses of cosmetic compositions comprising a black tea extract from any source, with the exception of black tea from Mauritius, for caring for the skin, scalp and appendages, and more particularly for protecting the skin from external aggression and oxidation, combating the signs of (Continued)

skin ageing, increasing photoprotection, lightening the skin and improving skin hydration.

19 Claims, 1 Drawing Sheet

(51) Int. Cl.

| | |
|---|---|
| ***A61Q 19/00*** | (2006.01) |
| ***A61Q 19/02*** | (2006.01) |
| ***A61Q 19/08*** | (2006.01) |

(56) References Cited

FOREIGN PATENT DOCUMENTS

| | | | |
|---|---|---|---|
| JP | 2006191924 | * | 7/2006 |
| JP | 2017-197476 | | 11/2017 |
| KR | 10-2012-0089407 | | 8/2012 |
| KR | 10-2016-0021734 | | 2/2016 |
| KR | 10-2018-0125828 | | 11/2018 |
| WO | WO2006111666 | | 10/2006 |
| WO | WO 2013092117 A2 | | 6/2013 |

OTHER PUBLICATIONS

Duke, J. A., Handbook of Energy Crops, 1983, Purdue University (Unpublished) https://hort.purdue.edu/newcrop/duke_energy/Camellia_sinensis.html.
J. Zeng et al., Molecules, 2018, 23, 2394.
Antioxidant potential and radical scavenging activity of different fermentation degree tea leaves extracts.
Antioxidant activity of various extracts of old tea leaves and black tea wastes (*Camellia sinensis* L.).
Liang Zhang, Comprehensive Reviews in Food Science and Food Safety, vol. 18, 2019.

* cited by examiner

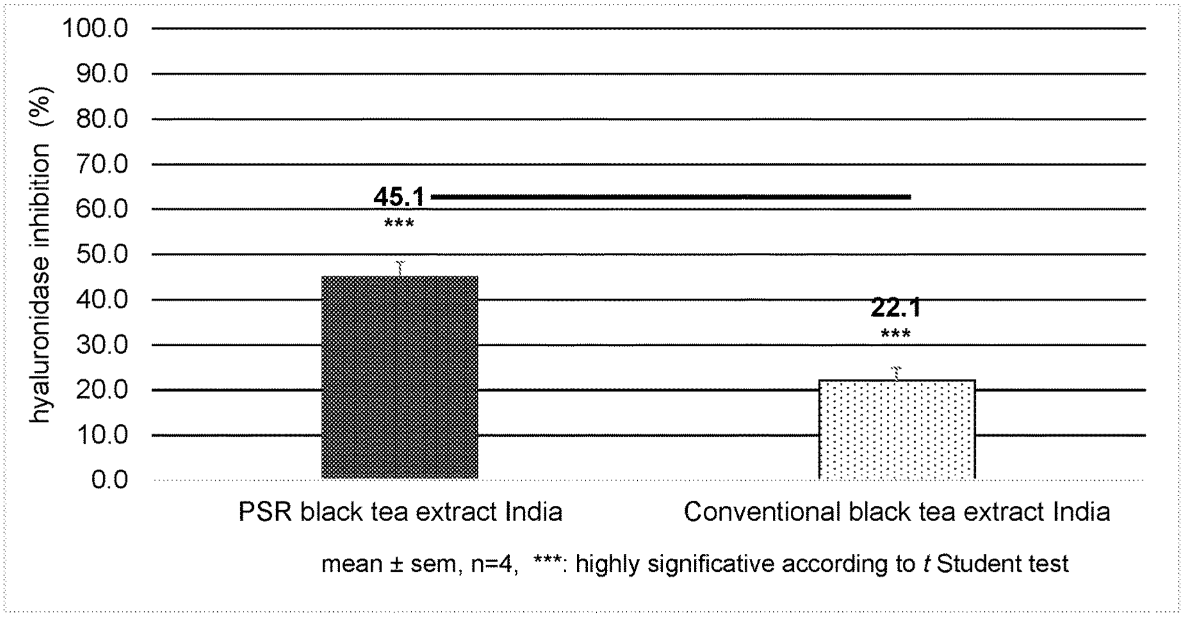
100.0
90.0
80.0
70.0
60.0
50.0
40.0
30.0
20.0
10.0
0.0
hyaluronidase inhibition (%)
45.1
***
22.1
***
PSR black tea extract India
Conventional black tea extract India
mean ± sem, n=4, ***: highly significative according to t Student test

BLACK TEA LEAF EXTRACT, COMPOSITIONS CONTAINING SAME, AND COSMETIC USES THEREOF

TECHNICAL FIELD

The present application relates to the field of cosmetics and more particularly to active agents of natural origin used in the preparation of cosmetic formulations to improve the appearance of the skin or to protect it.

The present application relates to an extract of black tea (*Camellia sinensis*) enriched in small RNAs, sugars, phenolic compounds, organic acids, amino acids and theanine, and to a process for preparing such an extract. The present application also relates to cosmetic compositions comprising such an extract. The present application further relates to cosmetic uses of compositions comprising an extract of black tea from any source, with the exception of black tea from Mauritius, for caring for the skin, scalp and appendages, and more particularly for protecting the skin from external aggression and oxidation, combating the signs of skin ageing, increasing photoprotection, lightening the skin and improving skin hydration.

TECHNICAL BACKGROUND OF THE INVENTION

The *Camellia sinensis* species, commonly known as the tea plant, comprises three botanical varieties: *Camellia sinensis* var. *assamica, Camellia sinensis* var. *sinensis* (Yunnan) and *Camellia sinensis* var. *Cambodiensis.*

The leaves of the tea plant (*Camellia sinensis*) are used to make different types of tea. It is the treatment applied to the harvested leaves that determines the type of tea obtained. Green tea has little or no oxidation, white tea is slightly oxidised, oolong tea is moderately oxidised (between 10% and 75%) and black tea is completely oxidised.

The environment in which the plant grows has an impact on its metabolism and influences the synthesis of phytomolecules. The plant's adaptation to its environment is the result of fine epigenetic regulation, which also involves the expression of small RNAs capable of rapidly regulating the expression of the plant's genes, thereby enabling it to adapt to stress and the environment.

Therefore, the season, the place of cultivation and the type of leaves harvested influence the chemical composition of black tea. For example, the buds and youngest leaves have the highest polyphenol content. These contain around 15% in dry weight of catechins, including 10% EGCG (Liang Zhang, Comprehensive Reviews in Food Science and Food Safety, Vol. 18, 2019), whereas this content is smaller in the older, lower leaves.

On average, fresh *Camellia sinensis* tea leaves from Assam in India contain 22.2% total polyphenols, including up to 15% catechins, 17.2% protein, 4.3% theine, 27% fibre, 0.5% starch and 3.5% reducing sugars (Duke, J. A., Handbook of Energy Crops, 1983, Purdue University, Unpublished.

Black tea is known for its health benefits, which are attributed to its high concentration of antioxidant molecules and other compounds that reduce inflammation and the risk of chronic diseases.

On average, black tea contains around 10.2 mg/g of catechins, 28.54 mg/g of theine, 1 mg/g of theobromine, 10.70 mg/g of theaflavins and 0.65 mg/g of theanine, but the quantities can vary considerably (Liang Zhang, Comprehensive Reviews in Food Science and Food Safety, Vol. 18, 2019).

Black tea is defined in the present application as tea from leaves of the species *Camellia sinensis* which have undergone complete oxidation. Black tea can be prepared using traditional or mechanised methods, which have in common a pre-drying or withering stage, followed by shredding or rolling of the leaves, the aim of which is to break the cells and release the enzymes responsible for oxidation, in particular polyphenol oxidase. The oxidation of black tea takes place when the polyphenols contained in the cell vacuoles come into contact with the degrading enzymes. The chemical reaction that takes place transforms the tea's catechins mainly into theaflavins and thearubigin. The chlorophyll is also transformed into pheophytin, which turns the tea black. Oxidation takes place in a hot, very humid atmosphere. Oxidation is then stopped by heating the leaves to 90° C.

Numerous tea leaf extracts have been described in the literature, in particular for their richness in phenolic compounds, including catechins. Most extraction methods in the prior art use organic solvents for their ability to extract catechin-type polyphenols (WO2006/111666, KR2016021734A, KR2018125828A). The extracts obtained are rich in polyphenols and flavonoids but contain little or no phenolic molecules such as phenolic acids, or organic molecules such as sugars, amino acids or oligo-ribonucleotides. Indeed, molecules such as sugars, amino acids or oligo-ribonucleotides are best extracted by polar solvents and ideally by aqueous solutions. Therefore, all of these phytomolecules, which are known to have beneficial effects on the skin, are not effectively extracted by the tea leaf extraction methods described in the prior art.

User demand for cosmetic products that are as natural as possible but with equivalent or even better efficacy than synthetic products is increasing rapidly. In the present application, the extracts described are 100% natural in order to meet consumer requirements.

One problem that the invention sets out to solve is to provide a new aqueous extract of black tea that meets the requirements of today's cosmetics market in terms of naturalness criteria and yet has remarkable biological efficacy and is non-toxic.

Too high a concentration of phenolic compounds such as catechins can cause phototoxicity or limit the stability of the extract over time. For example, the main form of catechin present in green tea, epigallocatechin gallate (EGCG), is highly unstable in aqueous solution. Under the effect of various factors such as oxygen, sunlight or changes in temperature or pH, it degrades, giving rise to superoxides and oxidised products. This leads to the formation of dimers responsible for the browning of solutions (J. Zeng et al. Molecules 2018, 23, 2394).

The extracts described in the present application have an original composition of phenolic compounds compared with the extracts described in the prior art. The concentration of phenolic compounds is significantly lower, is mainly composed of phenolic acids and contains very little of the main tea polyphenol, i.e., catechins. Furthermore, the extracts described in the present application are also stable over time and non-toxic.

Another problem that the invention sets out to solve is to provide a new aqueous extract of black tea enriched with compounds known to be effective on the skin, such as sugars, organic acids, amino acids, theine and theanine, as well as small RNAs.

The inventors have developed a new black tea extract specifically enriched in small RNAs, sugars, phenolic and organic compounds, organic acids, amino acids and theanine, obtained by a process that does not have the disadvantages of prior art processes, such as the use of potentially toxic detergents and solvents, for cosmetic use.

The extract thus obtained can be used in cosmetics to care for the skin, scalp and appendages, to obtain multiple benefits and more particularly to protect the skin from external aggression and oxidation, combat the signs of skin ageing, increase photoprotection, lighten the skin, improve skin hydration, reinforce the barrier function and soothe the skin.

SUMMARY OF THE INVENTION

The invention firstly relates to an extract of black tea leaves of the species *Camellia sinensis* comprising from 10 to 350 mg/kg of small RNAs with a length of at most 150 nucleotides, comprising at most 150 mg/kg of catechins, preferably at most 120 mg/kg of catechins and even more preferably at most 30 mg/kg of catechins.

The above extract can be obtained by the following production process, which the invention relates to secondly and which comprises the following steps:

a. placing previously ground black tea leaves of the *Camellia sinensis* species in water;
b. adding phytic acid;
c. adjusting the pH to a value between 10 and 11;
d. keeping the mixture under agitation for at least one hour at a temperature of between 4° and 80° C.;
e. purifying the mixture obtained in c) to eliminate the residual solid plant matter and collecting the filtrate;
f. adjusting the pH to a value between 6 and 8;
g. treating the mixture with powdered activated carbon;
h. filtering to remove the activated carbon and collect the filtrate;
i. treating the filtrate with polyvinylpolypyrrolidones (PVPP);
j. filtering to remove the PVPP and collect the filtrate;
k. checking the pH of the filtrate and readjusting it, if necessary, to a value between 6 and 6.5.
l. optionally, diluting the extract in a physiologically acceptable solvent and adjusting its pH to a value of between 5.8 and 6.7, preferably between 6.0 and 6.5, to obtain a diluted extract with a dry weight of between 4 and 20 g/kg.

The invention thirdly relates to a composition comprising, as active agent, an effective amount of the diluted aqueous extract of black tea leaves described herein, and a physiologically acceptable medium.

The invention fourthly relates to the cosmetic use of a composition comprising, as active agent, an effective amount of the diluted aqueous extract of black tea leaves described in this application, excluding black tea from Mauritius, and a physiologically acceptable medium for caring for the skin, scalp and appendages, and more particularly for protecting the skin from external aggression and oxidation, combating the signs of skin ageing, increasing photoprotection, lightening the skin, or improving skin hydration.

BRIEF DESCRIPTION OF THE DRAWINGS

The invention and the advantages arising therefrom will be better understood upon reading the description and the non-limiting embodiments which follow, illustrated with reference to the appended FIGURE in which:

FIG. 1 shows an evaluation of the hyaluronidase inhibitory activity of the various tea extracts from India obtained according to examples 1 and 2 by measuring turbidity.

DETAILED DESCRIPTION OF THE INVENTION

The inventors have developed a new extract of black tea (*Camellia sinensis*) enriched in small RNAs, sugars, phenolic and organic compounds, organic acids, amino acids and theanine, obtained by a process that does not have the disadvantages of prior art processes, such as the use of potentially toxic detergents and solvents, in cosmetics.

The inventors have also developed a process for enriching the extract with small RNAs, which are molecules known to be involved in epigenetic regulation and described for their beneficial activities on the skin. The extract is devoid of DNA, which is not known for its beneficial biological properties on the skin and can lead to a certain instability of the extract.

Definitions

All terms used in this application have the most widely known meaning or the meaning indicated below:

The term "black tea" means whole, dry, fully oxidised leaves of the *Camellia sinensis* species from any geographical origin.

The term "black tea from Mauritius" or "black tea from Mauritius" refers to tea grown, harvested and processed on plantations in Mauritius.

The term "tea from India" or "black tea from India" refers to tea grown, harvested and processed on tea plantations in India.

The term "black tea extract" or "black tea leaf extract" means an aqueous extract of black tea leaves of the species *Camellia sinensis* comprising from 10 to 350 mg/kg of small RNAs no more than 150 nucleotides long, free from DNA, comprising no more than 150 mg/kg of catechins, preferably no more than 120 mg/kg of catechins and even more preferably no more than 30 mg/kg of catechins.

The term "crude black tea extract" means that the extract obtained by the process described in this application has not been diluted.

The term "small RNAs" or "RNAs of small molecular weight", or "small RNAs no more than 150 nucleotides long" means non-coding RNAs (ribonucleic acids) of small molecular weight, no more than 150 nucleotides long, such as all types of small single- and/or double-stranded non-messenger RNA, for example microRNA, interfering RNA, introns, small nuclear RNA or any RNA fragment originating from the plant and extracted by the process described in this application. Thus, RNA fragments that are purified, of known sequences or synthesised do not fall within this definition.

The term "organic acids" we mean α-hydroxy acids (or AHAs), i.e. carboxylic acids derived from the sugars contained in tea leaves, such as lactic, malic, tartaric, succinic and uronic acids.

The term "phenolic compounds" means molecules of plant origin that have at least one phenolic-type aromatic ring bearing one or more hydroxyl groups, such as phenolic acids, polyphenols and flavonoids such as catechins. Phenolic compounds are known to be powerful antioxidant molecules, both in the plant and for cosmetic use. These secondary plant metabolites are also produced by plants as defensive mechanisms during biotic or abiotic stress.

The term "DNA-free" means that black tea extract contains no DNA. This has been demonstrated by a DNAse test, an enzyme that specifically degrades DNA and not RNA. The electrophoretic profile after DNase action is not modified, which demonstrates that the nucleic acid present in the extract is not sensitive to DNase and is therefore not DNA.

The term "sugars" means all types of sugars present in plants, such as monosaccharides like glucose or fructose, but also oligosaccharides and polysaccharides. As a general rule, polysaccharides contain more than ten monosaccharide units, while oligosaccharides contain between three and ten monosaccharide units.

The term "phytomolecules of interest" means all the molecules present in the tea extracts of the invention and in particular small RNAs with a maximum length of 150 nucleotides, sugars, phenolic compounds, organic acids, amino acids, theine and theanine.

Catechins are flavonoid polyphenols belonging to the catechin family, such as catechin (C), epicatechin (EC), epigallocatechin (EGC), gallocatechin (GC), catechin gallate (CG), gallocatechin gallate (GCG), epigallocatechin gallate (EGCG) and epicatechin gallate (ECG).

When a range of values is described, the limits of this range must be understood as explicitly including all the intermediate values of the range. For example, a range of values between 1% and 10% should be understood as including 1%, 2%, 3%, 4%, 5%, 6%, 7%, 8%, 9%, and 10%, as well as all decimal values between 1% and 10%.

Numerical percentage values are percentages by weight, i.e. the weight of a compound relative to the total weight of the intended mixture, unless otherwise specified.

The compositions described herein may "comprise", "consist of" or "consist substantially of" the essential compounds or optional ingredients.

The term "consist substantially of" means that the composition or component may include additional ingredients, but only if the additional ingredients do not alter the basic or novel characteristics of the composition or use described in this application.

The term "topical application" means applying or spreading the extract according to the invention, or a composition containing same, on the surface of the skin or a mucous membrane.

The term "skin" refers to the healthy skin of the face, particularly around the eyes and mouth, the nose, the forehead, the neck and the hands, as well as the skin of the whole body.

The term "scalp" means the healthy skin covering the skull, including the hair follicles and the inter-follicular skin spaces.

The term "appendages" refers to the products of hair follicles (hair, eyelashes and body hair) and nails, i.e. the keratin-rich appendages of the skin.

The term "lightening the skin" means reducing the intensity of skin colour linked to the melanin content of the epidermis, either evenly or locally by acting on pigmentary disorders such as age spots or senile lentigos.

The term "effective quantity" means the minimum quantity of extract according to the invention which is necessary to obtain at least one of the desired biological activities or to protect the skin from external aggression and oxidation, combat the signs of skin ageing, increase photoprotection, lighten the skin and improve skin hydration, without this quantity being toxic.

The term "skin hydration" refers to the water content and distribution in the upper layers of the epidermis.

The term "improved skin hydration" refers to any improvement in changes to the external appearance of the skin due to dehydration, such as dryness, tightness and discomfort, whether this is due to internal or external factors, such as adverse environmental conditions.

The term "signs of skin ageing" refers to all changes in the external appearance of the skin due to ageing, such as wrinkles and fine lines, cracks, bags under the eyes, dark circles, withering, loss of elasticity, firmness and/or toning of the skin, but also any internal changes to the skin which do not systematically result in a modified external appearance such as, for example, thinning of the skin, or any internal damage to the skin resulting from environmental stresses such as pollution and solar radiation including UV rays.

The term "signs of skin ageing" also includes pigmentation disorders such as senile lentigo or solar lentigo.

The term "external stresses" means solar radiation, including visible light, UV and infrared radiation, pollution, which may come from the ambient atmosphere outside or inside homes and includes particles of various sizes (10 μm for PM10, 2.5 μm for PM 2.5, or less than 100 nm for ultrafine particles) as well as a number of chemical elements (volatile organic compounds, polycyclic aromatic hydrocarbons, heavy metals, etc.).

The term "improving the appearance of the skin" means that the skin texture appears finer, the luminosity more intense and the complexion more even.

The term "physiologically acceptable" means a medium composed of at least one excipient, solvent or solvent mixture, suitable for contact with the outer layers of the skin or mucous membranes, without toxicity, irritation, undue allergic response or similar or intolerance reaction, and proportionate to a reasonable benefit/risk ratio.

It is understood that the invention relates to mammals and more particularly human beings.

Black Tea Extract

The invention firstly relates to an extract of black tea of the species *Camellia sinensis* comprising from 10 to 350 mg/kg of small RNAs with a length of at most 150 nucleotides, at most 150 mg/kg of catechins, preferably at most 120 mg/kg of catechins and even more preferably at most 30 mg/kg of catechins.

Advantageously, the black tea extract, in particular from India, contains traces of catechins, i.e. a maximum of 0.001% of catechins relative to the dry weight of the extract, or even more advantageously contains no catechins.

Advantageously, the black tea extract comprises from 0.030 to 5 g/kg of phenolic compounds.

The black tea extract preferably has a dry weight of 4 to 30 g/kg and comprises from 0.2 to 10 g/kg of sugars, from 0.010 to 3 g/kg of total amino acids, from 0.010 to 2 g/kg of theine and from 0.010 to 2 g/kg of theanine. Even more preferably, the black tea extract is aqueous, amber to dark amber in colour, has a dry weight of 4 to 30 g/kg and comprises from 0.2 to 10 g/kg of sugars, from 0.030 to 2 g/kg of organic acids, from 0.010 to 3 g/kg of total amino acids, from 0.030 to 5 g/kg of phenolic compounds including a maximum of 150 mg/kg of catechins, from 0.010 to 2 g/kg of theine and from 0.010 to 2 g/kg of theanine and from 10 to 350 mg/kg of small RNAs of a maximum length of 150 nucleotides, by weight of the total weight of the extract.

Moreover, the black tea extract contains no DNA (deoxyribonucleic acid).

In a particular embodiment, the black tea extract comes from Mauritius and has a dry weight of 5 to 30 g/kg, comprises from 0.5 to 10 g/kg of total sugars, from 0.050 to 2 g/kg of total organic acids, from 0.050 to 2 g/kg of amino acids, from 0.100 to 5 g/kg of total phenolic compounds including a maximum of 50 mg/kg of catechins, from 0.010 to 2 g/kg of theine and 0.010 to 2 g/kg of theanine and from 50 to 350 mg/kg of small molecular weight RNA with a maximum length of 150 nucleotides.

In an advantageous embodiment, the black tea extract is diluted in a physiologically acceptable solvent for cosmetic use. The dilution is carried out to adjust the dry weight of the extract to a value of between 4 and 20 g/kg.

The physiologically acceptable solvent is chosen from glycerol, ethanol, propanediol, butylene glycol, as well as their natural version, dipropylene glycol, ethoxylated or propoxylated diglycols, cyclic polyols or any mixture of these solvents.

Advantageously, the physiologically acceptable solvent is chosen from butylene glycol, propanediol or glycerine obtained from plants (natural version).

Preferably, the black tea extract is diluted in 30 to 50% butylene glycol, or 30 to 50% propanediol or 30 to 70% glycerine. When the solvent is glycerine, the black tea extract is preferably diluted in 70% glycerine.

Preferably, the black tea extract is diluted in propanediol obtained from the plant so that the diluted extract has a final propanediol concentration of 30% or 50%.

Preferably, the black tea leaf extract has been diluted in a physiologically acceptable solvent, has a dry weight of between 4 and 20 g/kg and comprises by weight of the total weight of the diluted extract, from 10 to 250 mg/kg of small molecular weight RNA with a length of at most 150 nucleotides, from 0.2 to 5 g/kg of sugars, from 0.010 to 2 g/kg of amino acids, from 0.030 to 3 g/kg of phenolic compounds including at most 120 mg/kg of catechins, from 0.010 to 1 g/kg of theine, and from 0.010 to 1 g/kg of theanine.

More preferably, the extract of black tea leaves thus diluted has a dry weight of between 4 and 20 g/kg and comprises, by weight of the total weight of the diluted extract, from 10 to 250 mg/kg of small molecular weight RNA with a maximum length of 150 nucleotides, from 0.2 to 5 g/kg of sugars, from 0.030 to 1 g/kg of organic acids, from 0.010 to 2 g/kg of amino acids, from 0.030 to 3 g/kg of phenolic compounds including a maximum of 120 mg/kg of catechins, from 0.010 to 1 g/kg of theine, from 0.010 to 1 g/kg of theanine, and is DNA-free.

When it comes from Mauritius and the diluted extract contains a final propanediol concentration of 30%, the black tea extract thus diluted has a dry weight of between 6 and 20 g/kg, and contains from 50 to 250 mg/kg of small molecular weight RNA with a maximum length of 150 nucleotides, from 0.8 to 5 g/kg of sugars, from 0.2 to 1 g/kg of organic acids, from 0.2 to 1 g/kg of amino acids, and from 0.5 to 3 g/kg of phenolic compounds, including a maximum of 30 mg/kg of catechins, from 0.10 to 100 mg/Kg of theine, from 0.010 to 300 mg/Kg of theanine, and is DNA-free.

Preferably black tea extract from Mauritius contains no catechins.

When it comes from India and the diluted extract contains a final propanediol concentration of 30%, the black tea extract thus diluted has a dry weight of between 4 and 12 g/kg, and contains from 10 to 100 mg/kg of small molecular weight RNA with a maximum length of 150 nucleotides, from 0.2 to 3 g/kg of sugars, from 0.030 to 0.5 g/kg of organic acids, from 0.030 to 0.3 g/kg of amino acids, and from 0.050 to 2 g/kg of phenolic compounds, including a maximum of 30 mg/kg of catechins, from 0.050 to 500 mg/Kg of theine, from 0.010 to 300 mg/kg of theanine, and is DNA-free.

The black tea extract described in this application thus comprises a wide range of phytomolecules with beneficial effects on the skin, without presenting any risk of skin irritation or other damage to health.

For example, sugars play an active role in moisturising the upper layers of the epidermis, thereby helping to resist external aggression, without having any undesirable effects. The tea extracts of the invention contain more particularly mono- and polysaccharides.

*Camellia sinensis* is a member of the Theaceae family, which produces theine, a powerful natural insecticide. Theine is also known as caffeine, 1,3,7-trimethylxanthine or methyltheobromine. In addition to its recognised effects on the nervous system and cardiovascular system, theine also has beneficial effects on the skin, in particular on sagging skin.

The plant also produces theanine, a non-protein amino acid which accounts for 50% of the total quantity of amino acids present in tea.

The black tea extract described in this application also contains phenolic compounds, such as polyphenols, phenolic acids and flavonoids such as catechins, but this family of molecules has been partially removed by treatment with carbon and PVPP. This relative depletion in phenolic compounds means that the product is more stable over time and a non-phototoxic extract is obtained.

Black tea extract also contains organic acids. Organic acids are molecules involved in the Krebs cycle, a metabolic process crucial to cellular respiration. Certain organic acids, such as malic and lactic acids, are known as alpha-hydroxy acids (AHAs), which are renowned for their anti-ageing effect on the skin, improving the appearance and texture of the skin.

In a particular embodiment, the diluted black tea extract contains a maximum of 1.5 g/kg of phenolic compounds, including a maximum of 120 mg/kg of catechins.

In another particular embodiment, the diluted black tea extract contains a maximum of 1.2 g/kg of phenolic compounds, including a maximum of 30 mg/kg of catechins.

In a particular embodiment, the diluted black tea extract contains a maximum of 3 g/kg of phenolic compounds and contains traces of catechins at a maximum of 0.001% of catechins based on the dry weight of the black tea extract from India, or even no catechins for black tea extract from India or Mauritius.

In another particular embodiment, the diluted black tea extract contains a maximum of 100 mg/kg of phenolic compounds and contains traces of catechins at a maximum of 0.001% of catechins relative to the dry weight of the black tea extract from India, or even no catechins for black tea extract from India or Mauritius.

In yet another embodiment, the diluted black tea extract contains a maximum of 50 mg/kg of phenolic compounds and contains traces of catechins of a maximum of 0.001% of catechins relative to the dry weight of the black tea extract from India, or even no catechins in the case of black tea extract from India or Mauritius.

All the black tea extracts described in this part of the application can be obtained by the extraction process described below.

Extraction Process

Classically described ribonucleic acid (RNA) extraction protocols use solvents unsuitable for cosmetic use (e.g. Brown, R. A. M., Epis, M. R., Horsham, J. L. et al. Total RNA extraction from tissues for microRNA and target gene expression analysis: not all kits are created equal. BMC Biotechnol 18, 16 (2018)). These methods aim to obtain completely purified nucleic acids (RNA or DNA), i.e. free from any other molecule of interest such as secondary metabolites, vitamins, sugars or even peptides, which are of cosmetic interest.

FR2831168 describes a process for obtaining a plant extract rich in nucleic acids (DNA and RNA). The process uses cellulolytic enzymes.

Also known from the prior art are patent documents EP1723958 and WO03101376, which describe a composition for topical application comprising a synthetic double-stranded RNA oligonucleotide 12 to 40 nucleotides long, of known sequence and having a siRNA (short interfering) function.

Document FR 1502361 (also published under number WO2017084958) describes a process for obtaining an aqueous plant extract enriched in low molecular weight ribonucleic acids (RNA) for preparing cosmetic compositions. The process uses EDTA at a concentration of between 2 and 15 mM.

The process described in this application has a low environmental impact in that it uses an aqueous solution and phytic acid, a naturally occurring molecule, as the extraction solvent.

The process described here makes it possible to obtain a black tea extract of 100% natural origin while maintaining good extraction efficiency of the phytomolecules contained in the plant.

The black tea extract described in the first part of this description is advantageously obtained by the extraction process described below.

The black tea leaves used in this process are dried, whole or reduced to powder.

When they are whole, they are ground to a powder beforehand.

In a first step a) of the process, the powdered black tea leaves are mixed with water. The water used is distilled or demineralised water or water rich in mineral salts and/or trace elements. The preferred water is distilled water.

In step a), the plant matter/water ratio is advantageously between 1% and 20%, preferably between 2 and 10% and even more preferably between 2 and 5%.

The mixture is preferably stirred.

In step b) phytic acid is added to the tea-water mixture from step a).

Phytic acid is a chelating agent naturally present in the casing of seeds such as cereals and legumes. It weakens and destroys the pecto-cellulosic membranes of plant cells by sequestering, through complexation, divalent ions such as calcium ions, which form ionic bridges between the pectin molecules surrounding the cellulose microfibrils. This has the effect of promoting the release of the cell content during extraction. The phytic acid treatment step in a basic medium is essential to enrich the extract in small molecular weight RNA and also to ensure a better extraction yield of the other phytomolecules of interest, namely sugars, amino acids, phenolic compounds, organic acids as well as theine and theanine.

The phytic acid used in the process is in the form of sodium, calcium or sometimes magnesium salts.

Preferably, the phytic acid used is a phytic acid powder in sodium salt form. Preferably it is used at a concentration of between 1 and 10 mM, preferably between 1 and 5 mM and even more preferably at a concentration of 3 mM.

It is particularly advantageous to use a concentration of phytic acid in sodium salt form of 3 mM.

In step c), the pH is adjusted to a basic value of between 10 and 11 by adding sodium hydroxide (NaOH). During step c) it is essential that the pH is basic, between 10 and 11. Preferably, the pH is adjusted to a value between 10.3 and 10.8. In fact, this pH level, combined with the action of phytic acid, causes destructuration of the cell membrane, including the nuclear membrane, lysis of the plant cells and denaturation of the DNA (the 2 strands of the double helix are separated).

Step d), extraction by alkaline lysis in the presence of phytic acid, preferably lasts at least 1 hour, at a temperature of between 40 and 80° C. Preferably the step lasts 1 hour. Advantageously, the step is carried out at a temperature of between 60° C. and 80° C. Even more preferably, the step is carried out at 80° C. During this step, the mixture is advantageously stirred moderately.

Checking the pH shows that it remains basic and stabilises between 9 and 11 at the end of step d).

In step e), the mixture obtained in d) is purified so as to eliminate the residual solids and recover the soluble part which constitutes the aqueous crude extract according to the invention.

Any method known to a person skilled in the art may be used to carry out this purification step. Preferably, the mixture is filtered directly on filters with a porosity greater than or equal to 30 μm so as to collect the filtrate. The mixture obtained in d) can also be centrifuged at low speed, for example for at least 10 min at 4000 g, so as to sediment the residual plant matter in the pellet and recover the aqueous crude extract in the supernatant.

In step f), the pH is adjusted to between 6 and 8. This acidification step causes the DNA to undergo abrupt renaturation (re-pairing of the double helix strands). However, chromosomal DNA, which is very long, does not manage to re-pair completely and forms insoluble tangles that will be eliminated later. Smaller, much shorter RNAs, on the other hand, remain in solution.

In step g), powdered activated carbon is added to the mixture. Preferably a mixture of two different types of carbon is used, in a proportion of 0.1 to 1% (weight/weight), and preferably a proportion of 0.25% (weight/weight) of each of the two types of activated carbon to increase decolourisation. The activated carbons are selected for their ability to deplete the extract of polyphenols, which are mainly responsible for the colour of the extract. This stage lasts from 15 minutes to 1 hour, preferably 30 minutes, at a temperature of between 4° and 50° C. with stirring for optimum results.

In step h), the mixture obtained in step g) is filtered to remove the carbon particles using filters with a porosity greater than or equal to 30 μm. A clarified filtrate is obtained.

In step i), the filtrate obtained in step h) is brought into contact with powdered PVPP in order to continue the removal of phenolic compounds such as high molecular weight polyphenols, such as tannins, which have not been retained by the activated carbons. Preferably, PVPPs are used in a proportion of between 0.5% and 3% (weight/weight), and preferably in a proportion of between 1% and 10%.

This step may last between 10 and 30 minutes, and preferably ten minutes, at a temperature of between room temperature and 50° C., with stirring.

In step j) the mixture obtained in step i) is clarified by filtration on filters with a porosity greater than 25 μm, followed by filtration using a filter with a porosity of 0.8 μm. This step eliminates the PVPP particles. The filtrate is collected.

The process described herein, and in particular steps g) to j), makes it possible to obtain an extract which contains traces, i.e. a maximum of 0.001% of catechins relative to the dry weight of the extract, or even no catechins, epicatechins or epigallocatechins. This was demonstrated by analyses of the extract using thin layer chromatography.

In step k), the pH of the mixture obtained in step j) is then adjusted to a value of between 6 and 6.5. A crude black tea extract is then obtained.

The pH is adjusted by adding a solution of hydrochloric acid (HCl) or any other equivalent acid compatible with cosmetic use, such as citric acid. Adjusting the pH to between 6 and 6.5 is an essential step in the process described in this application to keep low molecular weight RNAs in suspension and prevent precipitation of phytochemical compounds of interest such as sugars, phenolic compounds, organic acids, amino acids, theine and theanine.

The extraction process described above thus makes it possible to obtain an aqueous crude extract of black tea leaves of the species *Camellia sinensis* having a dry weight of 5 to 30 g/kg and comprising, by weight of the total weight of the extract, from 0.5 to 10 g/kg of sugars, from 0.050 to 2 g/kg of organic acids, from 0,030 to 3 g/kg of amino acids, from 0.050 to 5 g/kg of phenolic compounds including a maximum of 150 mg/kg of catechins, from 0.020 to 2 g/kg of theine, from 0.020 to 2 g/kg of theanine and from 50 to 350 mg/kg of small molecular weight RNA with a length of a maximum of 150 nucleotides and is free from DNA.

The present invention therefore also relates to an aqueous crude extract of black tea leaves of the species *Camellia sinensis*, obtainable by the process described above.

The extract obtained in step k) may optionally be diluted with a physiologically acceptable solvent in order to increase its stability and preservation over time. A diluted extract is then obtained.

The extract is diluted to obtain a dry weight of between 4 and 20 g/kg, and its pH is adjusted to between 5.8 and 6.5, preferably between 6.0 and 6.5. This step improves the product's stability over time.

The physiologically acceptable solvent may be chosen from the following solvents: water, glycerol, ethanol, propanediol, butylene glycol, as well as their natural version, dipropylene glycol, ethoxylated or propoxylated diglycols, cyclic polyols or any mixture of these solvents.

Preferably, ethanol, butylene glycol, propanediol and glycerine are plant-derived solvents (natural version).

Advantageously, the physiologically acceptable solvent is chosen from butylene glycol, propanediol or glycerine obtained from plants.

Butylene glycol or propanediol stabilises the extract and prevents the phytocompounds from precipitating over the long term. Glycerine, when used at a concentration of at least 70%, has the same properties. These solvents are also recognised for their bacteriostatic and even bactericidal or fungicidal properties, which also contribute to the long-term preservation and stability of the extract. Extract diluted in this way can be kept for at least twelve months. This aspect was validated by a study which, after inoculation of the extract with different types of microorganisms, measured its capacity to block the growth of microorganisms. The diluted extract can be kept for at least twelve months.

In a particularly preferred embodiment, the crude black tea extract can be mixed with 30 to 50% butylene glycol, or 30 to 50% propanediol or 30 to 70% glycerine.

When glycerine is used, it is preferably used at 70%.

Preferably, the black tea extract is diluted in propanediol obtained from the plant so that the diluted extract has a final propanediol concentration of 30% or 50%.

The aqueous extract of black tea leaves thus diluted has a dry weight of between 4 and 20 g/kg and comprises, by weight of the total weight of the diluted extract, from 10 to 250 mg/kg of small molecular weight RNA of a maximum length of 150 nucleotides, from 0.2 to 5 g/kg of sugars, from 0.030 to 1 g/kg of organic acids, from 0.010 to 2 g/kg of amino acids, from 0.030 to 3 g/kg of phenolic compounds including a maximum of 120 mg/kg of catechins, from 0.010 to 1 g/kg of theine, from 0.010 to 1 g/kg of theanine and is DNA-free. In a preferred embodiment, the black tea comes from Mauritius or India.

The aqueous extract of black tea leaves described in the above paragraph can be used directly to prepare the cosmetic composition of the invention.

Alternatively, the crude black tea extract obtained in step k) can also be dehydrated to obtain a dry extract in powder form. Any method known to the skilled person for dehydrating the extract can be used, for example freeze-drying.

The invention relates thirdly to a cosmetic composition comprising, as active agent, an effective amount of a diluted extract of black tea, obtained according to the process described above, and a physiologically acceptable medium.

Advantageously, black tea extract is added in a physiologically acceptable medium at a concentration of 0.05 to 5% by weight relative to the total weight of the composition, preferably at a concentration of 0.1 to 2.5% by weight relative to the total weight of the composition.

The composition of the present application is formulated to be applied by any suitable route, in particular orally, or topically externally, and the formulation of the compositions will be adapted by a person skilled in the art.

Preferably, the composition of the present application is in a form suitable for topical application. This composition must therefore contain a physiologically acceptable medium, i.e. compatible with the skin and the appendages, without any risk of discomfort during application.

The composition may in particular be in the form of an aqueous, hydroalcoholic or oily solution or gel, an oil-in-water, water-in-oil emulsion or multiple emulsions; they may also be in the form of suspensions, or powders, suitable for application to the skin, mucous membranes, lips and/or hair.

The composition may be more or less viscous and also have the appearance of a cream, lotion, fluid, milk, serum, ointment, gel, paste, balm or foam. It can also be in solid form, such as a stick, or applied to the skin as an aerosol.

Examples of physiologically acceptable media commonly used in the field of application under consideration are adjuvants required for formulation, such as solvents, thickeners, gelling agents, diluents, emulsifiers, antioxidants, colouring agents, sun filters, self-tanning agents, pigments, fillers, preservatives, perfumes, odour absorbers, essential oils, vitamins, essential fatty acids, surfactants, film-forming polymers, esters, vegetable oils or butters, etc.

In all cases, a person skilled in the art will ensure that these adjuvants and their proportions are chosen in such a way as not to impair the advantageous properties sought in the composition according to the invention. These adjuvants may, for example, each correspond to 0.01 to 20% of the total weight of the composition. When the composition according to the invention is an emulsion, the fatty phase may represent from 2 to 90% by weight and preferably from 5 to 30% by weight relative to the total weight of the composition. The emulsifiers and co-emulsifiers used in the composition are chosen from those conventionally used in the field in question. For example, they may be used in a proportion ranging from 0.3 to 30% by weight relative to the total weight of the composition.

According to another advantageous embodiment, the black tea extract can be encapsulated or included in a cosmetic vector such as liposomes or any other nanocapsule or microcapsule used in the cosmetics field, or adsorbed onto powdery organic polymers or mineral supports such as talcs and bentonites.

Advantageously, the composition may comprise, in addition to the active agent, i.e. a black tea extract, at least one other active agent with cosmetic effects similar and/or complementary to those of the invention.

For example, the additional active agent(s) may be chosen from: anti-ageing agents, firming agents, lightening agents, moisturising agents, draining agents, microcirculation-promoting agents, exfoliating agents, desquamating agents, extracellular-matrix-stimulating agents, energy-metabolism-activating agents, antibacterial agents, antifungal agents, soothing agents, anti-free-radical agents, anti-UV agents, anti-acne agents, anti-inflammatory agents, anaesthetic agents, agents that induce a warming sensation, agents that induce a cooling sensation, and slimming agents.

Such additional active agents may be selected from the groups comprising:

- vitamin A, in particular retinoic acid, retinol, retinol propionate and retinol palmitate;
- vitamin B3 and more particularly niacinamide and tocopherol nicotinate;
- vitamin B5, vitamin B6, vitamin B12, panthenol;
- vitamin C, in particular ascorbic acid, ascorbyl glucoside, ascorbyl tetrapalmitate, magnesium and sodium ascorbyl phosphate;
- vitamins E, F, H, K, PP, coenzyme Q10;
- metalloproteinase inhibitors, or a TIMP activator;
- DHEA, its precursors and derivatives;
- amino acids such as arginine, ornithine, hydroxyproline, hydroxyproline dipalmitate, palmitoylglycine, hydroxylysine, methionine and its derivatives, N-acylated amino acid compounds;
- natural or synthetic peptides, including di-, tri-, tetra-, penta- and hexapeptides and their lipophilic derivatives, isomeric and complexed with other species such as a metal ion (for example copper, zinc, manganese, magnesium, and others). Examples include peptides commercially known as MATRIXYL®, ARGIRELINE®, CHRONOGEN™, LAMINIXYL IS™, PEPTIDE Q10™, COLLAXYL™ (patent FR2827170, ASHLAND®), PEPTIDE VINCI 01™ (patent FR2837098, ASHLAND®), PEPTIDE VINCI 02™ (patent FR2841781, ASHLAND®), ATPeptide™ (patent FR2846883, ASHLAND®) or the synthetic peptide with sequence Arg-Gly-Ser-NH2, marketed under the name ATPeptide™ by ASHLAND®;
- *Artemia salina* extract, marketed under the name GP4G™ (FR2817748, ASHLAND®);
- plant peptide extracts such as flax extracts (Lipigenin™, patent FR2956818, ASHLAND®), soya extracts, spelt extracts, vine extracts, rapeseed extracts, flax extracts, rice extracts, maize extracts, pea extracts;
- yeast extracts, for example Dynagen™, (patent FR2951946, ASHLAND®) or Actopontine™ (patent FR2944526, ASHLAND®);
- dehydroacetic acid (DHA);
- phytosterols of synthetic or natural origin;
- salicylic acid and its derivatives, alpha- and beta-hydroxy acids, silanols;
- amino sugars: glucosamine, D-glucosamine, N-acetyl glucosamine, N-acetyl-D-glucosamine, mannosamine, N-acetyl mannosamine, galactosamine, N-acetyl galactosamine;
- extracts of polyphenols, isoflavones and flavonoids, such as grape extracts, pine extracts and olive extracts;
- lipids such as ceramides or phospholipids, oils of animal origin such as squalene or squalane; vegetable oils, such as sweet almond oil, copra oil, castor oil, jojoba oil, olive oil, rapeseed oil, groundnut oil, sunflower oil, wheat germ oil, maize germ oil, soya oil cotton, alfalfa, poppy, pumpkin, evening primrose, millet, barley, rye, safflower, passionflower, hazelnut, palm, apricot kernel, avocado, calendula; ethoxylated vegetable oils, shea butter, cocoa butter, babassu butter;
- all UV screens and sun filters;
- cyclic AMP and its derivatives, adenylate cyclase enzyme activating agents and phosphodiesterase enzyme inhibiting agents, Centella *asiatica* extract, asiaticoside and asiatic acid, methyl xanthines, theophylline, theobromine, forskolin, esculin and esculoside, ACE inhibitors, Val-Trp peptide, neuropeptide Y inhibitor, enkephalin, *Ginkgo biloba* extract, *dioscorea* extract, rutin, yerba mate extract, guarana extract, oligosaccharides, polysaccharides, carnitine, ivy extract, fucus extract, hydrolysed Prunella vulgaris extract, hydrolysed *Celosia cristata* extract, *Anogeissus leiocarpus* extract, *Manihot utilissima* leaf extract, palmitoylcarnitine, carnosine, taurine, elderberry extract, seaweed extracts such as Palmaria *Palmata* extract;
- hyaluronic acid or sodium hyaluronate and all its fractions and promoters;
- menthol and menthyl lactate and other active agents with a fresh effect;
- aloe vera, bisabolol, allantoin and other active agents with a soothing effect;
- vanillyl butyl ether and other active agents with a heating effect;
- benzoyl peroxide and other anti-acne active agents.

In a particular embodiment of the invention, the cosmetic composition comprises, as active agent, an effective amount of an extract of black tea from any source, excluding black tea from Mauritius, obtained according to the process described above, and a physiologically acceptable medium.

The invention fourthly relates to the cosmetic use of a previously described composition comprising an extract of black tea from any source, excluding black tea from Mauritius, for caring for the skin, scalp and appendages, and more particularly for protecting the skin from external aggression and oxidation, combating the signs of skin ageing, increasing photoprotection, lightening the skin and improving skin hydration.

The term "cosmetic use" means that the product is intended for use on individuals with healthy skin, scalp or appendages.

The skin is an organ made up of several layers (dermis, epidermis and stratum corneum), covering the entire surface of the body and providing protection from external aggression, sensory, immune, metabolic and thermoregulatory functions, as well as acting as a barrier to limit dehydration.

The appearance of the skin can be altered by internal changes (intrinsic ageing, diseases and hormonal changes such as pregnancy) or external changes (environmental factors such as pollution, sunlight, pathogens, temperature variations, etc.). All of these alterations affect not only the skin, but also the keratinous appendages, or appendages such as the hair, eyelashes, eyebrows, nails and hair.

EXAMPLES

By way of illustration, examples of how the process according to the invention can be carried out are described below.

Example 1: Preparation of Extracts of Black Tea (*Camellia sinensis*) from India and Mauritius Enriched in Small RNAs According to the Process of the Invention In order to take account of the plant's great capacity to adapt to its environment, black tea extracts (all from the species *Camellia sinensis*) from different geographical origins were used to implement the process of the invention as described in this example.

Extracts of black tea from Mauritius and black tea from India were prepared.

Mauritius is crowned by mountain ranges, varying in height from 300 to 800 m above sea level. The land rises from the coastal plains to a central plateau where it reaches a height of 670 m. The island's climate makes it an ideal place for growing tea. Black tea from Mauritius is tea grown, harvested and processed on plantations in Mauritius.

Indian tea is tea grown, harvested and processed on tea plantations at altitudes of between 1200 and 2200 metres in India.

In a first step a) the black tea leaves, previously ground to a coarse powder, are weighted to represent 3% of the raw material used in the process, i.e. 30 g for 1 kg. The quantity of distilled water added is 968 g.

The tea leaves and water mixture is stirred to improve extraction of the phytomolecules of interest, thanks to better exchange between the solid matter, the tea, and the aqueous extraction solution.

In step b), phytic acid at 2 g/l (i.e. 3 mM final) is added to the mixtures of water and ground tea leaf.

In step c), the pH is adjusted to 10.5 to optimise extraction and enrich the extract with small molecular weight RNA and various phytomolecules.

In step d) the mixture is heated for 1 hour at 80° C. with moderate stirring.

In step e) the mixture is filtered using filters with a porosity of 30 μm, to separate the solid matter from the filtrate. Three sequential filtrations are then carried out using filters of decreasing porosity in order to clarify the plant extract until filtration at 3 μm porosity.

Step f) The pH of the filtrate collected in step e), which is greater than 9 on average, is adjusted to between 6 and 8 to achieve an optimum pH for the activated carbon treatment that follows.

Step g) Treatment with a duo of NORIT® SX+ and CAI activated carbons is carried out to decolourise the extract, in particular by removing polyphenols. 2.5 g of each type of carbon is added per litre of extract. The treatment lasts thirty minutes at a temperature of between 4° and 50° C.

Step h): The carbons are removed by passing the extract through filters with a porosity of 30 μm.

In step i) a second decolourisation treatment of the filtrate obtained in g) is carried out by adding (PVPP) powder. 10 g of PVPP are added per litre of extract in order to remove some of the tannins contained in the extract. The treatment is carried out for 10 minutes at a temperature of between 4° and 50° C.

In step j), sequential filtrations on filters of decreasing porosity are then carried out in order to remove the PVPP from the plant extract. An initial 30 μm filtration allows the PVPP to be retained, followed by successive filtrations down to a porosity of 0.8 μm in order to clarify the extract.

In step k) the pH is checked and then adjusted to a value of between 6 and 6.5 using a citric acid or hydrochloric acid solution.

The aqueous crude black tea extract thus obtained from black tea from Mauritius has a dry weight of 10.8 g/kg. Physico-chemical analysis shows that the extract obtained has a concentration of 3.3 g/kg of total sugars, 550 mg/kg of total organic acids, 340 mg/kg of amino acids, 1.2 g/kg of total phenolic compounds and 260 mg/kg of small molecular weight RNA with a maximum length of 150 nucleotides.

The aqueous crude black tea extract obtained from black tea from India has a dry weight of 7.8 g/kg. Physico-chemical analysis shows that the extract obtained has a concentration of 1.2 g/kg total sugars, 280 g/kg total organic acids, 230 mg/kg amino acids, 0.51 g/kg total phenolic compounds and 160 mg/kg small molecular weight RNA with a maximum length of 150 nucleotides.

The extracts obtained in step k) are diluted with plant-derived propanediol to obtain a final concentration of 30% propanediol and 70% tea extract. This solvent, which is physiologically acceptable for cosmetic use, stabilises the product and increases its preservation over time. The result is a diluted extract with a pH adjusted to between 6.0 and 6.5.

The composition of the crude aqueous extracts after addition of 30% propanediol is given in Table 1 below.

TABLE 1

| | PSR black tea extract Mauritius | PSR black tea extract India |
|---|---|---|
| Dry weight (g/Kg) | 7.4 | 5.6 |
| Total sugars (g/kg) | 1.2 | 0.5 |
| Total organic acids (mg/kg) | 310 | 155 |
| Amino acids (mg/kg) | 262 | 120 |
| Total phenolic compounds (mg/kg) | 770 | 310 |
| RNA up to 150 nucleotides long (mg/kg) | 154 | 85 |

The diluted tea extracts obtained using the process described in this example are referred to as PSR (Plant Small RNAs) tea in the tables or FIGURE presented in this application.

Example 2: Preparation of a Comparative Extract of Black Tea (*Camellia sinensis*) Using a Conventional Extraction Method The aim of the process used in example 2 is to prepare a control extract to obtain comparative analytical data in relation to the tea extracts obtained by the process of the invention (example 1).

The so-called conventional extraction method chosen is optimal for extracting the different types of phenolic compounds and other polar molecules such as sugars and amino acids, making it a good reference process for making comparisons with the process of the invention applied in example 1.

In the first stage, to produce 1 kg of extract, the same teas as in example 1, from Mauritius and India, were used (from the *Camellia sinensis* species).

The dried black tea leaves, previously ground to a coarse powder, are weighed to represent 3% of the raw material used in the process, i.e. 30 g for 1 kg, which is mixed with 970 g of distilled water.

The extraction pH is not adjusted and is between 5 and 7.

The mixture is then heated for 1 hour at 45° C. with stirring.

The mixture is then filtered using filters with a porosity of 30 μm to separate the solid matter from the filtrate. Sequential filtrations on filters of decreasing porosity are then carried out to clarify the plant extract until filtration at 1 μm porosity.

At the end of this stage, the extract is treated with carbon to decolourise it, in particular by removing polyphenols. 2.5 g of each carbon is added per litre of extract. The treatment lasts thirty minutes at a temperature of between 4° and 50° C. and a pH of between 6 and 8. A 30 μm filtration is carried out to remove the carbons from the extract.

A second decolourisation treatment was then carried out by adding PVPP powder. 10 g of PVPP were added to the extract to remove some of the tannins contained in the extract. The treatment lasted 10 minutes at a temperature of between 4° and 50° C. Sequential filtrations on filters of decreasing porosity are then carried out to clarify the plant extract down to 0.2 μm filtration.

The pH is checked and then adjusted to between 6 and 6.5 using a solution of citric acid, hydrochloric acid or sodium hydroxide.

The extract of raw black tea from Mauritius obtained has a dry weight of 7 g/kg. Physico-chemical analysis shows that the extract obtained has a concentration of 0.9 g/kg of total sugars, 310 mg/kg of total organic acids, 190 mg/kg of amino acids and 270 mg/kg of total phenolic compounds.

The aqueous crude black tea extract from India obtained has a dry weight of 4 g/kg. Physico-chemical analysis shows that the extract obtained has a concentration of 0.8 g/kg of total sugars, 190 mg/kg of total organic acids, 140 mg/kg of amino acids and 170 mg/kg of total phenolic compounds.

The extract is then diluted with plant-derived propanediol, a physiologically acceptable cosmetic solvent, to obtain a final concentration of 30% propanediol and 70% tea extract. The composition of the extracts obtained by the conventional method is given in table 2 below.

TABLE 2

| | Conventional black tea extract Mauritius | Conventional black tea extract India |
|---|---|---|
| Dry weight (g/Kg) | 5 | 2.8 |
| Total sugars (g/kg) | 0.5 | 0.4 |
| Total organic acids (mg/kg) | 210 | 132 |
| Amino acids (mg/kg) | 112 | 80 |
| Total phenolic compounds (mg/kg) | 180 | 120 |
| RNA up to 150 nucleotides long (mg/kg) | n.d. | n.d. |

Example 3; Quantification of the Various Components of the Diluted Black Tea Extracts Obtained in Examples 1 and 2 and Assessment of the Microbiological Stability of the Extract from Example 1

The dry weight of each extract, obtained according to example 1 (process of the invention) or according to example 2 (conventional process) was measured after 12 hours of steaming at 105° C.

The PSR extracts obtained by the process of example 1 (the process of the invention) have a higher dry weight than the tea extracts obtained by the conventional process, which means that the extraction yield is higher in the process of example 1 (see table 3).

TABLE 3

| | PSR black tea extract Mauritius | PSR black tea extract India | Conventional black tea extract Mauritius | Conventional black tea extract India |
|---|---|---|---|---|
| Dry weight (g/Kg) | 7.4 | 5.6 | 5 | 2.8 |
| Extraction yield (%) | 26 | 19 | 16 | 9.3 |

The total sugar content of the tea extracts from examples 1 and 2 was determined by spectrophotometric assay based on an adaptation of the assay described by Dubois et al. (1956) (Dubois et al., "Méthode colorimétrique pour la détermination des sucres et des substances apparentées", Anal. Chem, 1956, 28 (3), 350-356). The black tea extracts from examples 1 and 2 are dissolved in concentrated sulphuric acid and then reacted with phenol to form a coloured complex. The absorbance of the complex is read on the spectrophotometer at 490 nm. The sugar content is determined using a standard glucose curve.

The analysis shows a higher concentration of sugars in the black tea extracts from all sources obtained by the process in Example 1 compared with the sugar concentration in the extract obtained by the conventional method in Example 2. The results are shown in Table 4.

TABLE 4

| | PSR black tea extract Mauritius | PSR black tea extract India | Conventional black tea extract Mauritius | Conventional black tea extract India |
|---|---|---|---|---|
| Total sugars (g/kg) | 1.2 | 0.5 | 0.5 | 0.4 |

The total amino acid content of the black tea extracts in examples 1 and 2 was determined spectrophotometrically using a protocol published by Moore S. and Stein WH. (1948) (Moore, S. and Stein, W. H. (1948) Photometris Ninhydrin Method for Use in the Chromatography of Amino Acids. The Journal of Biological Chemistry, 176, 367-388).

The free amino acid content of the extract was assessed by the formation of a coloured complex following the disruption of the amine and carboxyl functions by the reagent ninhydrin. The absorbance of the complex was read at 570 nm. The total amino acid content was determined using a standard curve based on a pool of amino acids.

The analysis shows a higher concentration of amino acids in the black tea PSR extracts obtained by the process of the invention in example 1 compared with the concentration of amino acids in the extracts obtained by the conventional method in example 2.

TABLE 5

| | PSR black tea extract Mauritius | PSR black tea extract India | Conventional black tea extract Mauritius | Conventional black tea extract India |
|---|---|---|---|---|
| Total amino acids (mg/kg) | 262 | 120 | 112 | 80 |

The total phenolic content of the black tea extracts in examples 1 and 2 was determined by the Folin-Ciocalteu spectrophotometric method (Singleton et al., Analysis of total phenols and other oxidative and antioxidant substrates using the Folin-Ciocalteu reagent, 1999, 299:152). The polyphenol compounds present in the sample react with the Folin-Ciocalteu reagent to give a blue colour. The absorbance of the sample is read on the spectrophotometer at 760 nm. The total polyphenol concentration is expressed in gallic acid equivalents using a standard gallic acid curve.

The analysis shows a higher concentration of phenolic compounds in the extracts obtained using the process described in the invention for all black tea origins compared with the conventional extraction process, as described in table 6.

TABLE 6

| | PSR black tea extract Mauritius | PSR black tea extract India | Conventional black tea extract Mauritius | Conventional black tea extract India |
|---|---|---|---|---|
| Total phenolic compounds (mg/kg) | 770 | 310 | 180 | 120 |
| % (weight/weight) Total phenolic compounds/ extracted dry weight | 13 | 5.5 | 5 | 4.2 |

The characterisation and quantification of the organic acids contained in the black tea extracts from examples 1 and 2 was carried out using high-performance liquid chromatography, coupled with an ACQUITY Qda mass detector (WATERS). The samples were separated on an EC 150/4.6 Nucleoshell RP 18plus-5 μm column (150×4.6 mm) (Macherey Nagel: 763236.46) by an Agilent 1260 HPLC system (Agilent Technologies). The flow rate was 0.3 ml/min. The mobile phase consisted of a solution of 0.01% formic acid (HCOOH) (A) and acetonitrile.

Organic acids were identified by comparing the retention times and mass spectral peaks of the sample with a standard. Quantitative estimation of the organic acids was based on the area of the chromatographic peaks compared with the areas of the standards.

HPLC-MS analysis thus shows that the black tea extracts from Mauritius or India obtained using the process of the invention have a higher total concentration of organic acids than the conventional extracts described in example 2, as described in table 7.

The analysis also shows that the black tea extracts obtained according to examples 1 and 2 contain different types of organic acids, as illustrated in table 7. Tartaric acid and uronic acids were not detected or were detected in very low quantities either in the PSR black tea extracts obtained according to example 1 or in the conventional extracts of example 2.

TABLE 7

| Type of extract | Lactic acid (mg/kg) | Succinic acid (mg/kg) | Malic acid (mg/kg) | Acid Tartar (mg/kg) | Uronic acid (mg/kg) |
|---|---|---|---|---|---|
| PSR black tea Mauritius | 143.3 | 6.9 | 57.9 | n.d. | 14 |
| PSR black tea India | 4.6 | 9.9 | 47.2 | 4.2 | n.d. |
| Conventional black tea extract Mauritius | 3.3 | 8.4 | 54 | n.d. | n.d. |
| Conventional black tea extract India | 17.1 | 3.5 | 34.6 | n.d. | 13.8 |

The theanine content of the black tea extracts from examples 1 and 2 was assessed by high-performance liquid chromatography, coupled with a UV (ultraviolet light) detector. The samples were separated on a 250 mm×4.6 mm×5 um Uptisphère C18-2 column (Interchim) by an Agilent 1200 HPLC system (Agilent Technologies). The flow rate was 0.4 ml/min. The mobile phase consisted of 0.1% phosphoric acid (H3PO4) in aqueous solution (A) and acetonitrile (ACN) (B).

Theanine was identified by comparing the retention time and the UV spectral peak of the sample with a standard. A quantitative estimate of theanine was made on the basis of the area of the chromatographic peaks compared with the area of the standard.

HPLC-UV analysis shows that the black tea extracts obtained according to example 1 contain theanine in equivalent quantities, and contain more than conventional extracts. The results are shown in Table 8.

TABLE 8

| | PSR black tea extract Mauritius | PSR black tea extract India | Conventional black tea extract Mauritius | Conventional black tea extract India |
|---|---|---|---|---|
| L-theanine (mg/kg) | 54 | 51 | 44 | 41 |

The assessment of the theine (or caffeine) content of the black tea extracts from examples 1 and 2 was carried out by high-performance liquid chromatography, coupled with a UV detector. The samples were separated on a 100 mm×4.6 mm×2.6 pm Uptisphere CS evolution C18-AQ column (Interchim) by an Agilent 1100 HPLC system (Agilent Technologies). The flow rate was 0.8 ml/min. The mobile phase consisted of 0.1% TFA (trifluoroacetic acids) in aqueous solution (A) and methanol (B).

The temperature was 25° C. The injection volume was 5 μl and the detection wavelength was set at 272 nm using a UV detector. The theine standard was purchased from Sigma-Aldrich. Theine identification was performed by comparing the retention times and UV spectral peaks of the sample with an authentic standard. A quantitative estimate of theine was made on the basis of the area of the chromatographic peaks compared with the area of the standard.

HPLC-UV analysis shows that all types of tea extract contain theine. The black tea extracts obtained by the conventional extraction mentioned in example 2 have a higher theine concentration than the extracts obtained using the process described herein. The results are shown in table 9.

TABLE 9

| | PSR black tea extract Mauritius | PSR black tea extract India | Conventional black tea extract Mauritius | Conventional black tea extract India |
|---|---|---|---|---|
| Theine (mg/kg) | 68 | 122 | 80 | 164 |
| % theine/extracted dry weight | 0.9 | 2.2 | 5.3 | 2.1 |

Total catechins were also quantified. Catechins exist in the form of several stereoisomers due to the presence of two asymmetric carbons. In nature, the most common isomers are (+)-catechin and (−)-epicatechin. The other two enantiomers are much rarer and their presence seems to be linked to enzymatic reactions or heat treatments. All samples were separated on a 100 mm×4.6 mm×2.6 pm Uptisphere CS evolution C18-AQ column (Interchim) using an Agilent 1100 HPLC system (Agilent Technologies). The flow rate was 0.8 ml/min. The mobile phase consisted of 0.1% TFA (trifluoroacetic acids) in aqueous solution (A) and methanol (B).

HPLC-UV analysis, which allows to quantify and identify the catechins contained in the various black tea extracts obtained according to examples 1 and 2 (process of the invention and so-called conventional process), shows that the black tea extracts obtained either by the process of the invention or by conventional extraction contain traces, i.e. a maximum of 0.001% of catechin-type polyphenols relative to the dry weight of the extract, or even no catechin-type polyphenols as shown in table 10 (n.d. means not determinable). This absence or low quantity of these molecules in the extracts can be explained by the fact that the carbon and PVPP treatment stages removed this type of compound. This confirms the effectiveness of the carbon treatment combined with PVPP in removing this type of molecule.

TABLE 10

| | PSR black tea extract Mauritius | PSR black tea extract India | Conventional black tea extract Mauritius | Conventional black tea extract India |
|---|---|---|---|---|
| Catechins (mg/kg) | n.d. | 28 | n.d. | n.d. |
| % catechins/ dry weight extract | 0 | 0.001 | 0 | 0 |

In addition, thin layer chromatography analyses showed that none of the tea extracts of the invention contained epicatechin or epigallocatechin.

The quantification and measurement of the size of low molecular weight RNAs was carried out using a miniaturised electrophoresis technique on microfluidic chips specifically designed for nucleic acid analysis, such as that of small molecular weight RNAs (Bioanalyzer 21000, Agilent). This method is used to determine the size and concentration of nucleic acids contained in an extract.

The small RNAs present in the tea extracts of the invention are in the form of a complex mixture of RNAs, the majority of which are between 25 and 150 nucleotides in size.

The results of the quantification by the Bioanalyzer show that the black tea extracts obtained by the process of example 1 enable small molecular weight RNAs to be extracted from the different types of tea as shown in table 11. Conversely, no small molecular weight RNA is detectable in conventional black tea extracts (n.d. means not determinable).

TABLE 11

| | PSR black tea extract Mauritius | PSR black tea extract India | Conventional extract black tea Mauritius | Conventional black tea extract India |
|---|---|---|---|---|
| Small RNAs (mg/Kg) | 154 | 85 | n.d. | n.d. |
| Small RNAs (% total dry extract) | 2.1 | 1.5 | 0 | 0 |

Evaluation of the Microbiological Stability of the Black Tea Extract According to Example 1

The stability of a black tea extract of Indian origin obtained according to example 1 was carried out according to the following protocol:

Inoculation was carried out on day 0 and day 21. Tests were carried out 48 h, 7 days, 14 days, 21 days and 28 days after inoculation. The culture medium for bacteria was tryptone-soya agar and for fungi dextrose-potato agar.

Standard temperature and time conditions, adapted to the types of microorganisms tested, were used.

Results

Raw (undiluted) black tea extract from India showed a contamination rate of over 100 CFU after a few days.

Extract of black tea from India diluted with propanediol to obtain a final concentration of 30% propanediol and 70% tea extract gives the results shown in Table 12.

TABLE 12

| Microorganism | Inoculum (cfu/g) | 48 h | 7 days | 14 days | 21 days | 28 days |
|---|---|---|---|---|---|---|
| *Staphylococcus aureus* | $4.5 \times 10^6$ | <10 | <10 | <10 | <10 | <10 |
| *Escherichia coli* *Pseudomonas aeruginosa* *Burkholderia cepacia* | $2.0 \times 10^6$ | <10 | <10 | <10 | <10 | <10 |
| *Candida albicans* *Aspergillus brasiliensis* | $2.5 \times 10^5$ | <10 | <10 | <10 | <10 | <10 |

Example 4: Evaluation of the Black Tea Extracts from Examples 1 and 2 for their Activity in Inhibiting an Enzyme, Hyaluronidase, in an In Vitro Test Concept The aim of this test is to demonstrate the inhibitory power of extracts from examples 1 and 2 from India on the enzymatic activity of hyaluronidase using a turbidity test. Hyaluronic acid is a glycosaminoglycan present in the dermis, capable of retaining a large quantity of water in the dermal extracellular matrix and in so doing is a major player in skin hydration. Hyaluronidase is an enzyme present in the skin which catalyses the breakdown of hyaluronic acid into mono- or disaccharides and smaller hyaluronic acid fragments. In the presence of acid albumin, hyaluronic acid is able to react to form a haze that can be measured using spectrophotometry at 600 nm. The inhibition of enzyme activity is therefore measured by analysing the turbidity levels of the samples after they have been brought into contact with the enzyme and its substrate.

Protocol

The enzyme is incubated with the extracts obtained according to examples 1 and 2 from India, so that the extract is at a final concentration of 1% in the reaction mixture, for 20 minutes at a temperature of 37° C., in a buffer at pH7, ideal conditions for enzymatic equilibrium. The enzyme substrate, hyaluronic acid, was added to the mixture at a concentration of 0.3 mg/ml. The mixture was slowly homogenised and then incubated for 45 minutes at 37° C. The hyaluronic acid remaining in the mixture was then brought into contact with an acid albumin solution and homogenised. The reaction time was 10 minutes, after which the transmittance was read at 600 nm using a spectrophotometer. The data are compared with those obtained with a negative inhibition control corresponding to the condition where the enzyme has degraded the substrate to 100%, corresponding to 100% enzyme activity.

Results

The extract of black tea from India prepared according to example 1 and tested at 1% showed a percentage inhibition of hyaluronidase of 45.1%. The tea extract from India prepared conventionally according to example 2 showed inhibition percentages of 22.1%. The results are illustrated in FIG. 1.

Conclusion

Tests to assess the inhibitory effect of extracts tested at 1% on the activity of hyaluronidase in vitro show that the black tea extract prepared according to example 1 (process of the invention) from India has a significantly stronger inhibitory power for the enzyme than the extract prepared according to a conventional process (example 2).

Example 5: Formula for an Anti-Ageing Mask

TABLE 13

| Ingredients (Brand name) | INCI | % w/w |
|---|---|---|
| | Phase A | |
| Purified water | Aqua | Qsp 100 |
| Tetrasodium EDTA | Tetrasodium EDTA | 0.05 |
| | Phase B | |
| N-Hance ™ HP40S guar | Hydroxypropyl Guar | 0.10 |
| | Phase C | |
| Lubrajel ™ DV Free hydrogel | Glycerin (and) Glyceryl Acrylate/Acrylic Acid Copolymer | 6.00 |
| | Phase D | |
| Si-Tec ™ GF 3096 silicone | Dimethicone (and) Dimethiconol | 12.00 |
| RapiThix ™ A-60 polymer | Sodium Polyacrylate (and) Hydrogenated Polydecene (and) Trideceth-6 | 2.40 |
| | Phase E | |
| Optiphen ™ Plus preservative | Phenoxyethanol (and) Caprylyl Glycol (and) Sorbic Acid | 1.50 |
| | Phase F | |
| Surfin* 96 | Alcohol Denat. | 3.50 |
| PF Cucumber & Aloe | Perfume/Fragrance | 0.50 |
| | Phase G | |
| Extract as per example 1, from India | Propanediol (and) *Camellia Sinensis* Leaf Extract | 1.00 |
| Achromaxyl ™ ISR biofunctional | Water/Aqua (and) Glycerin (and) Hydrolyzed Brassica Napus Seedcake Extract | 3.00 |
| Xirona Carribean Blue | Mica (and) CI 77891 (Titanium Dioxide) (and) Silica (and) Tin Oxide | 1.00 |

Preparation Process 1. at 25° C., homogenise phase A in the main container,
2. at 25° C., sprinkle into phase B and mix well until homogeneous;
3. at 25° C., add phase C and mix well until homogeneous;
4. pre-mix phase D in a separate beaker and add to the main container at 25° C.;
5. at 25° C., add phase E to the main container and mix well;
6. pre-mix phase F and add slowly. Mix well until homogeneous;
7. pre-mix phase G in a separate beaker and add to the main container until homogeneous;
8. stop at 25° C.

The composition thus takes the form of a creamy gel with shimmering green effects, with a pH of between 5.30 and 5.80 and a viscosity (DO) of 70,000-100,000 cps (Brookfield RVT/Spindle C/5 RPM/1 minute/25° C.).

Example 6: Serum Formula

TABLE 14

| Ingredients (Brand name) | INCI | % w/w |
|---|---|---|
| | Phase A | |
| Demineralised water | Aqua | 87.40 |
| Sodium Hyaluronate | Sodium Hyaluronate | 0.20 |
| RapiThix ™ A-60 polymer | Sodium Polyacrylate (and) Hydrogenated Polydecene (and) Trideceth-6 | 0.40 |

TABLE 14-continued

| Ingredients (Brand name) | INCI | % w/w |
|---|---|---|
| Lubrajel ™ DV hydrogel | Glycerin (and) Glyceryl Acrylate/Acrylic Acid Copolymer (and) Propylene Glycol | 6.00 |
| Lubrajel ™ Oil hydrogel | Glycerin (and) Glyceryl Acrylate/Acrylic Acid Copolymer (and) Propylene Glycol (and) PVM/MA Copolymer | 1.00 |
| Wacker-Belsil* DM 100 | Dimethicone | 2.00 |
| Cyclopentasiloxane NF | Cyclopentasiloxane | 0.50 |
| Extract as per example 1, origin India | Propanediol (and) *Camellia Sinensis* Leaf Extract | 1.00 |
| Optiphen ™ preservative | Phenoxyethanol (and) Caprylyl Glycol | 1.50 |

Preparation Process

1. Add water to the main container and start mixing with a hi-lo propeller blade;
2. Add the remaining ingredients, one at a time, stirring between each addition.

The composition thus takes the form of a smooth, semi-opaque serum with a pH of between 5.75 and 6.25 and a viscosity (DO) of 1,100-1,400 cps (Brookfield RVT/spindle 3/20 rpm/25° C./1 minute).

What is claimed is:

1. An extract of black tea leaves of species *Camellia sinensis* comprising from 10 to 350 mg/kg of small ribonucleic acids (RNAs) with a length of at most 150 nucleotides and at most 150 mg/kg of catechins, characterized in that the extract of black tea leaves of the species *Camelia sinensis* is obtained by a production process comprising:

a) placing previously ground black tea leaves in water to obtain a mixture;

b) adding phytic acid to the mixture obtained in a);

c) adjusting a pH of the mixture obtained in b) to a value between 10 and 11;

d) keeping the mixture obtained in c) under agitation for at least one hour at a temperature of between 4° and 80° C.;

e) purifying mixture obtained in c) to eliminate residual solid plant matter and collecting the resulting first filtrate;

f) adjusting a pH of the first filtrate to a value between 6 and 8;

g) treating the mixture obtained in f) with powdered activated carbon;

h) filtering to remove the activated carbon and collecting resulting second filtrate;

i) treating the second filtrate with polyvinylpolypyrrolidone (PVPP);

j) filtering to remove the PVPP and collecting resulting third filtrate;

k) checking a pH of the third filtrate and readjusting the pH of the third filtrate, if necessary, to a value between 6 and 6.5 to obtain an extract; and l) optionally, diluting the extract obtained in k) in a solvent and adjusting its pH to a value of between 5.8 and 6.5, to obtain a diluted extract with a dry weight of between 4 and 20 g/kg.

2. The extract of black tea leaves according to claim 1, wherein it contains traces of catechins, defined as a maximum of 0.001% of catechins relative to a dry weight of the extract or contains no catechins.

3. The extract of black tea leaves according to claim 1, wherein it comprises from 0.030 to 5 g/kg of phenolic compounds.

4. The extract of black tea leaves according to claim 1, wherein it has a dry weight of 4 to 30 g/kg and comprises from 0.2 to 10 g/kg of sugars, from 0.010 to 3 g/kg of total amino acids, from 0.010 to 2 g/kg of theine, and from 0.010 to 2 g/kg of theanine.

5. The extract of black tea leaves according to claim 1, wherein it has been diluted in the solvent, has a dry weight of between 4 and 20 g/kg and comprises, by weight of a total weight of the diluted extract, and comprises from 10 to 250 mg/kg of small molecular weight RNA with a length of at most 150 nucleotides, from 0.2 to 5 g/kg of sugars, from 0.010 to 2 g/kg of amino acids, from 0.030 to 3 g/kg of phenolic compounds including at most 120 mg/kg of catechins, from 0.010 to 1 g/kg of theine, and from 0.010 to 1 g/kg of theanine.

6. A composition comprising, as active agent, an effective amount of diluted black tea extract according to claim 5, and a medium.

7. The composition according to claim 6, wherein said active agent is present at a concentration of between 0.05 and 5% by weight of a total weight of the composition and the medium.

8. The composition according to claim 6, wherein it is formulated to be applied topically to skin, appendages, and a scalp.

9. The composition according to claim 6, wherein said active agent is an extract of black tea from any source, excluding black tea from Mauritius.

10. A method of cosmetic treatment, comprising applying the composition of claim 9 for caring for skin, a scalp, and appendages.

11. The method of cosmetic treatment according to claim 10 to obtain cosmetic benefits chosen from: protecting the skin from aggression and oxidation, combating signs of skin aging, increasing photoprotection, lightening the skin, or improving skin hydration.

12. The extract of black tea leaves according to claim 1, wherein the catechins are present in an amount of at most 30 mg/kg.

13. The extract of black tea leaves according to claim 1, wherein the extract is diluted in l) in the solvent and its pH adjusted to a value of between 6.0 and 6.5, to obtain the diluted extract with the dry weight of between 4 and 20 g/kg.

14. A process for obtaining an extract from leaves of black tea of species *Camellia sinensis* comprising from 10 to 350 mg/kg of small ribonucleic acids (RNAs) with a length of at most 150 nucleotides and at most 150 mg/kg of catechins, said process comprising:

a) placing previously ground black tea leaves in water to obtain a mixture;

b) adding phytic acid to the mixture obtained in a);

c) adjusting a pH of the mixture obtained in b) to a value between 10 and 11;

d) keeping the mixture obtained in c) under agitation for at least one hour at a temperature of between 4° and 80° C.;

e) purifying the mixture obtained in c) to eliminate residual solid plant matter and collecting resulting first filtrate;

f) adjusting a pH of the first filtrate to a value between 6 and 8;

g) treating the mixture obtained in f) with powdered activated carbon;

h) filtering to remove the activated carbon and collecting resulting second filtrate;

i) treating the second filtrate with polyvinylpolypyrrolidone (PVPP);

j) filtering to remove the PVPP and collecting resulting third filtrate;

k) checking a pH of the third filtrate and readjusting the pH of the third filtrate, if necessary, to a value between 6 and 6.5 to obtain an extract; and l) optionally, diluting the extract obtained in k) in a solvent and adjusting its pH to a value of between 5.8 and 6.5, to obtain a diluted extract with a dry weight of between 4 and 20 g/kg.

15. The process according to claim 14, wherein when the extract obtained in k) is diluted in the solvent is chosen from water, glycerol, ethanol, propanediol, butylene glycol, dipropylene glycol, ethoxylated or propoxylated diglycols, cyclic polyols, or any mixture of these solvents.

16. The process according to claim 14, wherein in a), the black tea leaves are placed in water, in a plant matter/water ratio of between 1% and 20%.

17. The process according to claim 14, wherein in b) the phytic acid is at a concentration of between 1 and 10 mM.

18. The process according to claim 14, wherein, in e), at least one filtration is carried out on filters with a porosity greater than or equal to 30 μm.

19. The process according to claim 14, wherein in j), sequential filtrations are carried out with filters of porosity greater than 25 μm, followed by filtration with a filter of porosity 0.8 μm.

* * * * *